United States Patent
Yamada (10) Patent No.: US 9,878,063 B2
(45) Date of Patent: Jan. 30, 2018

(54) DEODORIZING MASK (71) Applicant: TOAGOSEI CO., LTD., Minato-ku (JP)

(72) Inventor: Yoshinao Yamada, Nagoya (JP)

(73) Assignee: TOAGOSEI CO., LTD., Minato-ku (JP)

( * ) Notice: Subject to any disclaimer, the term of this patent is extended or adjusted under 35 U.S.C. 154(b) by 0 days.

(21) Appl. No.: 15/316,942

(22) PCT Filed: May 26, 2015

(86) PCT No.: PCT/JP2015/065141
§ 371 (c)(1),
(2) Date: Dec. 7, 2016

(87) PCT Pub. No.: WO2015/194334
PCT Pub. Date: Dec. 23, 2015

(65) Prior Publication Data
US 2017/0100503 A1   Apr. 13, 2017

(30) Foreign Application Priority Data
Jun. 20, 2014  (JP) ................................ 2014-127640

(51) Int. Cl.
A61L 9/01 (2006.01)
A61L 9/014 (2006.01)
A41D 13/11 (2006.01)
A62B 18/02 (2006.01)

(52) U.S. Cl.
CPC .......... *A61L 9/014* (2013.01); *A41D 13/1138* (2013.01); *A41D 13/1192* (2013.01); *A62B 18/02* (2013.01)

(58) Field of Classification Search
CPC ... A61L 19/01; A61L 19/014; A41D 13/1138; A41D 13/1192; A62B 18/02
USPC .......................................... 502/402
See application file for complete search history.

(56) References Cited

U.S. PATENT DOCUMENTS

2015/0056102 A1   2/2015  Yamada et al.

FOREIGN PATENT DOCUMENTS

| JP | 10-211294 A | 8/1998 |
|----|---|---|
| JP | 2003-93529 A | 4/2003 |
| JP | 3108929 U | 3/2005 |
| JP | 2005-95879 A | 4/2005 |
| JP | 2009-291284 A | 12/2009 |
| JP | 2012-187332 A | 10/2012 |
| WO | 2013/133195 A1 | 9/2013 |

OTHER PUBLICATIONS

International Search Report dated Jun. 23, 2015, in PCT/JP2015/065141, filed May 26, 2015.
Office Action dated Sep. 5, 2017, in Japanese Patent Application No. 2016-529203 (with English Machine Translation).

*Primary Examiner* — Edward Johnson
(74) *Attorney, Agent, or Firm* — Oblon, McClelland, Maier & Neustadt, L.L.P.

(57) ABSTRACT

The deodorizing mask of the present invention has a main body part that includes a deodorizing fiber layer containing a composite fiber having a chemical adsorption type deodorizer bonded to the surface of a fiber with an adhesive composition. The chemical adsorption type deodorizer is a component having at least one type selected from copper and zinc elements. The adhesive composition includes at least one type selected from polyester, poly vinyl alcohol, cellulose, starch, poly acrylamide, poly alkylene oxide and poly vinyl pyrrolidone.

7 Claims, 3 Drawing Sheets

DEODORIZING MASK

TECHNICAL FIELD

The present invention relates to a deodorizing mask excellent in deodorizing performance to a sulfur-based malodorous gas.

BACKGROUND ART

Conventionally, masks are used for preventing the invasion of a malodorous gas, fine particles or the like into the respiration organs. In particular, a mask for a malodorous gas commonly contains a deodorizer for adsorbing malodorous components. For example, a mask having a deodorizing fiber layer obtained using a sheet containing a fiber having a deodorizer bonded to a surface thereof, and a mask having a deodorizing fiber layer obtained using a sheet containing a fiber having a deodorizer partially exposed therefrom are known.

In recent years, deodorizing masks for various malodorous components are used, but it has become apparent that the characteristic odor arising from the mask itself may give unpleasant feeling, in addition to a breath odor of the wearer.

For example, Patent Document 1 discloses a form-reinforced mask including a mask main body and straps, and a tape-like cataplasm having an aroma and efficacy bonded to the backside, and a form-reinforced mask which bulges out to form a three-dimensional shape when the mask main body is expanded.

In addition, Patent Document 2 discloses an aroma mask including a synthetic resin film impregnated with a perfume, and a nonwoven fabric placed on at least one side of the resin film, the mask reducing unpleasantness caused by unpleasant odor during long-time or repeated use.

PRIOR TECHNICAL LITERATURE

Patent Literature

[Patent Document 1] JP-A 2012-187332
[Patent Document 2] JP-A Hei 10-211294

SUMMARY OF THE INVENTION

Problems that the Invention is to Solve

Fiber products such as a mask and filter are generally packaged (contained) after manufacture in bags and boxes made of paper, a resin film, or the like. Among the fiber products obtained by bonding a deodorizer to the fiber surface using a polymer adhesive, some emits an unpleasant odor (off-flavor), and the origin of the odor cannot be identified where it arises from the deodorizer, fibers, and adhesive composing the fiber product, and the package material when the fiber products are unpackaged.

The present invention is intended to provide a deodorizing mask that is excellent in deodorizing performance to a sulfur-based malodorous gas, the deodorizing mask having no unpleasant odor by itself, and is pleasantly used without causing unpleasant odor and color change, even when stored in an enclosed environment.

Means to Solve the Problems

The present invention is as follows.
1. A deodorizing mask comprising a main body part that includes a deodorizing fiber layer containing a composite fiber having a chemical adsorption type deodorizer bonded to a surface of a fiber with an adhesive composition, characterized in that the chemical adsorption type deodorizer is a component comprising at least one element selected from a copper element and a zinc element, and that the adhesive composition comprises at least one type selected from a polyester, a poly vinyl alcohol, a cellulose, a starch, a poly acrylamide, a poly alkylene oxide and a poly vinyl pyrrolidone.
2. The deodorizing mask according to 1 above, wherein the chemical adsorption type deodorizer is at least one component selected from an oxide comprising a copper element and a phosphate comprising a copper element.
3. The deodorizing mask according to 1 or 2 above, wherein a content of the chemical adsorption type deodorizer in the deodorizing fiber layer is not less than 1 $g/m^2$.
4. The deodorizing mask according to any one of 1 to 3 above, wherein a solid content of the adhesive composition and the chemical adsorption type deodorizer in the deodorizing fiber layer are respectively 10% to 90% by mass and 10% to 90% by mass based on 100% by mass of a total of these components.
5. The deodorizing mask according to any one of 1 to 4 above, wherein a fiber constituting the deodorizing fiber layer comprises a fiber including a polyethylene resin, and wherein a content ratio of the polyethylene resin is in a range from 10% to 80% by mass based on a total amount of fibers constituting the deodorizing fiber layer.
6. The deodorizing mask according to any one of 1 to 5 above, wherein the deodorizing fiber layer is a layer in which the chemical adsorption type deodorizer is joined to the surface of the fiber by padding method or dipping method.

In the present invention, a substance which is a cause of bad smell is referred to as "malodorous component", and a gas containing the malodorous component is referred to as "malodorous gas". A unit "ppm" with regard to the gas concentration is "ppm by volume". The "basis weight" is a mass per 1 $m^2$ ($g/m^2$) in the normal state, and the value measured by a method according to JIS L 1096: 2010. Further, the "air permeability" is a value measured by Frazier method according to JIS L 1096:2010.

Effect of the Invention

The deodorizing mask of the present invention is excellent in deodorizing performance to a sulfur-based malodorous gas since the mask includes a main body part having a specific deodorizing fiber layer. In addition, it has no unpleasant odor by itself, so it is pleasantly used with emitting no unpleasant odor and inhibiting color change even when stored in an enclosed environment. The deodorizing mask of the present invention is suitable for the use in places where a sulfur-based malodorous gas is emitted (for example, medical, care, and excretion sites, sewage treatment plants, garbage disposal sites (incineration sites), fertilizer plants, chemical plants, livestock farms, fishing ports, and animal-related facilities).

EMBODIMENTS FOR CARRYING OUT THE INVENTION

The present invention is a deodorizing mask that includes a main body part having a deodorizing fiber layer (hereinafter, referred to as "deodorizing fiber layer (L1)") containing a composite fiber having a chemical adsorption type deodorizer bonded to a surface of a fiber with an adhesive composition. The chemical adsorption type deodorizer (hereinafter, referred to as "chemical adsorption type deodorizer (X)") is a component containing at least one element selected from a copper element and having deodorizing performance to a sulfur-based malodorous gas including hydrogen sulfide, mercaptans, dimethyl disulfide, sulfur dioxide, or the like. The adhesive composition contains at least one type selected from a polyester, a poly vinyl alcohol, a cellulose, a starch, a poly acrylamide, a poly alkylene oxide and a poly vinyl pyrrolidone. A structure of the deodorizing mask of the present invention is not particularly limited. The mask may have a flat structure or a three-dimensional structure. In the three-dimensional case, the structure may be in pleated shape, omega pleated shape, or cup-like shape. (See, FIGS. 5, 6, and 7) The deodorizing fiber layer (L1) for the main body part is arranged to cover at least nose and mouth, and the size is the same as the main body part.

In the deodorizing mask, the main body part may further include, as will be described later, other deodorizing fiber layer (hereinafter, referred to as "deodorizing fiber layer (L2)") containing a chemical adsorption type deodorizer having deodorizing performance to other malodorous gas than the sulfur-based malodorous gas, a fiber layer containing a component other than a deodorizer, or a fiber layer (hereinafter, referred to as "fiber layer (L3)") consisting of fibers. In the case where the main body part has the deodorizing fiber layer (L2) or fiber layer (L3), these layers are preferably arranged so as to cover nose and mouth.

The deodorizing fiber layer (L1) is preferably consisting of a fiber aggregation that contains a composite fiber having fiber and a chemical adsorption type deodorizer (X) bonded to a surface of the fiber via an adhesive layer derived from an adhesive composition. The fiber aggregation may further contain a composite fiber having a fiber and the chemical adsorption type deodorizer (X) buried in the main body part of the fiber so as to expose the chemical adsorption type deodorizer (X), a fiber free from any deodorizer including the chemical adsorption type deodorizer (X) (an ordinary fiber), a fiber having other chemical adsorption type deodorizer, and the like.

The number of the deodorizing fiber layer (L1) included in the main body part may be one or more. When the number of the layers is two or more, the deodorizing fiber layer (L2) or fiber layer (L3) is preferably included between the deodorizing fiber layers (L1).

An average diameter of a fiber part of the composite fiber or ordinary fiber contained in the fiber aggregation constituting the deodorizing fiber layer (L1) is generally in a range from 5 to 30 µm, and preferably from 10 to 25 µm.

The fiber aggregation constituting the deodorizing fiber layer (L1) may be based on either a woven fabric, a nonwoven fabric, or a knitted cloth. The fiber aggregation preferably has a form of a nonwoven fabric since setting of a desired thickness is easy, a production cost is inexpensive, and permeability can be readily controlled.

The fiber in the nonwoven fabric is preferably a resin fiber. Examples of a resin constituting the resin fiber include a polyester, a polyethylene, a polypropylene, a poly vinyl chloride, a polyacrylic acid, a polyamide, a poly vinyl alcohol, a polyurethane, a poly vinyl ester, a polymethacrylic acid ester, a rayon, and the like. Among these resins, a polyester, a polyethylene, a polypropylene and a rayon are preferable from a viewpoint of adhesiveness by the adhesive composition, and a polyester, a polyethylene, and a polypropylene are more preferable. The nonwoven fabric may be an aggregation having a fiber containing only one type of a resin, an aggregation having a plural type of resin fibers, or an aggregation having a core-sheath type fiber containing a plural type of resin. The resin fiber may include publicly known additives for polymers, such as an antioxidant, a plasticizer, an antistatic agent, an antibacterial agent, a fungicide, a reinforcing agent and a stabilizer.

In the present invention, the deodorizing fiber layer (L1) is preferably a layer formed using a nonwoven fabric including a fiber containing a polyethylene resin in which a content ratio of the polyethylene resin is preferably in a range from 10% to 80% by mass, and more preferably from 20% to 70% by mass based on a total amount of fibers constituting the deodorizing fiber layer. As described above, the main body part may further include the deodorizing fiber layer (L2) or fiber layer (L3). In a case of a welding method, which is a common method for forming an integral main body part, an unpleasant odor may occur and adsorb to the fibers when fiber aggregations are welded at a temperature exceeding 150° C. The main body part preferably includes a polyethylene resin-containing fiber which can be welded at a temperature lower than 150° C.

When the fiber aggregation is in a form of a nonwoven fabric, the nonwoven fabric is preferably a nonwoven fabric interlacing by needle-punching method, water-jet interlacing method (spunlace method), or the like, a nonwoven fabric produced by thermal bonding method, and a nonwoven fabric produced by spun bonding method.

The chemical adsorption type deodorizer (X) is a component containing at least one element selected from a copper element and a zinc element. In the present invention, these components may be used singly or in combination of two or more types thereof.

Examples of the chemical adsorption type deodorizer (X) include a metal copper, a compound containing a copper element, a metal zinc, a compound containing a zinc element, and the like.

Examples of the compound containing a copper element include an oxide (including a composite oxide with other oxide); a hydroxide; a salt of inorganic acid such as phosphoric acid and sulfuric acid; a salt of organic acid such as acetic acid, oxalic acid, and acrylic acid; a complex; and the like. Among them, an oxide and a phosphate are preferable from a viewpoint of deodorizing performance to a sulfur-based malodorous gas. Particularly preferred are a CuO- .$SiO_2$ composite oxide and a $ZrCu(PO_4)_2 \cdot H_2O$ (copper zirconium phosphate hydrate). The latter compound can be obtained by reacting a layered zirconium phosphate $Zr(HPO_4)_2 \cdot H_2O$ with a divalent copper salt, and the reaction product is said to be a material in which a part of H atom in $HPO_4$ of the layered zirconium phosphate $Zr(HPO_4)_2 \cdot H_2O$ is remained or is substituted with Na atom.

Examples of the compound containing a zinc element include an oxide (including a composite oxide with other oxide); a hydroxide; a salt of inorganic acid such as phosphoric acid, sulfuric acid, and silicic acid; a salt of organic acid such as acetic acid, oxalic acid, and acrylic acid; a complex; and the like. Specific examples include zinc oxide, zinc aluminum oxide, zinc silicate, zinc aluminum silicate, layered zinc aluminosilicate, and the like. Among these, zinc oxide is preferable.

A shape of the chemical adsorption type deodorizer (X) is not particularly limited. Regarding the size of the chemical adsorption type deodorizer (X) in the form of grains, a median diameter measured by a laser diffraction type particle size distribution analyzer is preferably in a range from 0.05 to 100 µm, more preferably from 0.1 to 50 µm, and further preferably from 0.2 to 30 µm, from a viewpoint of the deodorizing efficiency. If the chemical adsorption type deodorizer (X) is too large, the surface area of the exposed deodorizer per unit mass is small, so that sufficient deodorizing effect may not be achieved, or sufficient permeability may not be achieved in the main body part including the deodorizing fiber layer (L1) when the desired basis weight is established.

An excellent deodorization effect can be obtained as the efficiency of contacting the chemical adsorption type deodorizer (X) with the malodorous component becomes higher, so that a specific surface area is preferably in a range from 10 to 800 $m^2/g$, and more preferably from 30 to 600 $m^2/g$. The specific surface area can be measured by BET method which calculates from a nitrogen adsorption amount.

A content of the chemical adsorption type deodorizer (X) in the deodorizing fiber layer (L1) is preferably 1 $g/m^2$ or more, more preferably 3 $g/m^2$ or more, and further preferably 5 $g/m^2$ or more. The upper limit is usually 30 $g/m^2$ since air permeability in the deodorizing fiber layer (L1) decreases as the content of the chemical adsorption type deodorizer (X) in the deodorizing fiber layer (L1) increases. In addition, a content ratio of the chemical adsorption type deodorizer (X) is preferably in a range from 2 to 60 parts by mass, more preferably from 5 to 50 parts by mass, and further preferably from 10 to 40 parts by mass based on 100 parts by mass of the fibers constituting the deodorizing fiber layer (L1).

The deodorizing mask of the present invention may be, as described above, in an embodiment in which the deodorizing fiber layer (L1) and deodorizing fiber layer (L2) containing other chemical adsorption type deodorizer are included. The deodorizing fiber layer (L1) may further contain other chemical adsorption type deodorizer, and may be prepared for other malodorous gases without deteriorating deodorizing effect to a sulfur-based malodorous gas. The deodorizing fiber layer (L1) or (L2) may include a composite fiber having other chemical adsorption type deodorizer bonded to a surface of a fiber, the deodorizer including a tetravalent metal phosphate, a zeolite and an amorphous composite oxide that are deodorizers for a malodorous gas containing a malodorous component such as ammonia and trimethylamine; hydrated zirconium oxide, zirconium oxide and a hydrotalcite-based compound that are deodorizers for a malodorous gas containing a malodorous component such as acetic acid and isovaleric acid; a hydrazine-based compound and an aminoguanidine salt that are deodorizers for a malodorous gas containing a malodorous component such as aldehyde; or the like.

The tetravalent metal phosphate is preferably a compound represented by the following general formula (1). The compound is insoluble or hardly soluble in water.

$$H_a M_b (PO_4)_c \cdot n H_2 O \tag{1}$$

(In the formula, M is a tetravalent metal atom, a, b and c are each an integer satisfying a formula: a+4b=3c, and n is 0 or a positive integer.)

Examples of M in the general formula (1) include Zr, Hf, Ti, Sn, and the like.

Preferable specific examples of the tetravalent metal phosphate include zirconium phosphate ($Zr(HPO_4)_2 \cdot H_2O$), hafnium phosphate, titanium phosphate, tin phosphate, and the like. There are crystalline substances having various crystal systems such as α type crystal, β type crystal, and γ type crystal, and an amorphous substance in these compounds, either of which is preferably used.

The zeolite is preferably a synthetic zeolite. The zeolite is insoluble or hardly soluble in water. There are various structures of the zeolite such as A type, X type, Y type, α type, β type, and ZSM-5, and either of the conventionally known zeolites can be used.

The amorphous composite oxide is a compound other than the above zeolite. The composite oxide is preferably an amorphous composite oxide constituted by at least two types selected from $Al_2O_3$, $SiO_2$, MgO, CaO, SrO, BaO, $ZrO_2$, $TiO_2$, $WO_2$, $CeO_2$, $Li_2O$, $Na_2O$, $K_2O$, and the like. The composite oxide is insoluble or hardly soluble in water. An amorphous composite oxide represented by $X_2O-Al_2O_3-SiO_2$ (X is at least one alkali metal atom selected from Na, K and Li) is particularly preferred since it is excellent in deodorizing performance. Being amorphous means no clear diffraction signals based on crystal face can be recognized when X-ray powder diffraction analysis is carried out, more specifically, high kurtosis (the so-called sharp) signal peak is not substantially appeared in the X-ray diffraction chart in which a diffraction angle is plotted at the transverse axis and a diffraction signal intensity is plotted at the vertical axis.

The hydrotalcite-based compound is a compound having a hydrotalcite structure, and is preferably represented by the following general formula (2). The compound is insoluble or hardly soluble in water.

$$M^1_{(1-x)} M^2_x (OH)_2 A^{n-(x/n)} \cdot m H_2 O \tag{2}$$

(In the formula, $M^1$ is a divalent metal atom, $M^2$ is a trivalent metal atom, x is a number larger than 0 and 0.5 or less, $A^{n-}$ is an n-valent anion such as carbonic acid ion and sulfuric acid ion, and m is a positive integer.)

As the hydrotalcite-based compound, magnesium-aluminum hydrotalcite is particularly preferred since it shows more excellent deodorization effect to an acidic gas. A calcined product of the hydrotalcite, i.e., a compound obtained by calcining the hydrotalcite compound at a temperature of about 500° C. or higher to remove a carboxylate or a hydroxyl group is also included in the hydrotalcite-based compound.

Examples of the hydrazine-based compound include adipic acid dihydrazide, carbohydrazide, succinic dihydrazide, and oxalic dihydrazide.

Examples of the aminoguanidine salt include aminoguanidine hydrochloride, aminoguanidine sulfate, aminoguanidine bicarbonate, and the like.

When the deodorizing fiber layer (L1) contains other chemical adsorption type deodorizer, a content ratio is not particularly limited and is preferably in a range from 10 to 100 parts by mass, more preferably from 20 to 90 parts by mass, and further preferably from 25 to 80 parts by mass based on 100 parts by mass of the chemical adsorption type deodorizer (X).

The deodorizer such as the chemical adsorption type deodorizer (X) is bonded to the fiber surface via an adhesive layer derived from the adhesive composition containing a specific polymer. The polymer is at least one type selected from a polyester, a poly vinyl alcohol, a cellulose, a starch, a poly acrylamide, a poly alkylene oxide and a poly vinyl pyrrolidone, and is preferably a polymer that is capable of preparing an aqueous dispersion or an aqueous solution. Since the deodorizing mask having the specific polymer does not emit unpleasant odor when stored in an enclosed environment, the mask can be pleasantly used thereafter. The polymer contained in the adhesive composition may be one or more.

The polyester may be an aromatic polyester or an aliphatic polyester. These polyesters may be combined. The polyester may be a saturated polyester or an unsaturated polyester. The polyester is preferably a saturated polyester composed of a polycondensate obtained using an acid component and a hydroxyl group-containing component. The polyester may be a polyester having a hydrophilic group such as $-SO_3H$, $-SO_3Na$, $-SO_3^-$, $-COOH$, $-COO^-$, $-OPO(OH)_2$, and $-OPO(OH)O^-$.

Examples of the acid component include terephthalic acid, isophthalic acid, orthophthalic acid, naphthalenedicarboxylic acid, 4,4'-diphenyl dicarboxylic acid, trimellitic acid, trimesic acid, pyromellitic acid, benzoic acid, p-oxy benzoic acid, p-(hydroxyethoxy)benzoic acid, succinic acid, adipic acid, azelaic acid, sebacic acid, glutaric acid, suberic acid, dodecane dicarboxylic acid, fumaric acid, maleic acid, itaconic acid, 1,4-cyclohexanedicarboxylic acid, 1,3-cyclohexanedicarboxylic acid, cyclobutane tetracarboxylic acid, dimethylolpropionic acid, tricyclodecane dicarboxylic acid, tetrahydroterephthalic acid, tetrahydroorthophthalic acid, hexahydroorthophthalic acid, methylester of these di, tri, or, tetracarboxylic acid, anhydride thereof, and the like.

Examples of the acid component having a hydrophilic group include a sulfonate-based compound such as 5-sodium sulfonate isophthalic acid, 5-ammonium sulfonate isophthalic acid, 4-sodium sulfonate isophthalic acid, 4-ammonium methylsulfonate isophthalic acid, 2-sodium sulfonate terephthalic acid, 5-potassium sulfonate isophthalic acid, 4-potassium sulfonate isophthalic acid, 2-potassium sulfonate terephthalic acid, and the like.

Examples of the hydroxyl group-containing component include ethylene glycol, diethylene glycol, triethylene glycol, tetraethylene glycol, propylene glycol, dipropylene glycol, 1,3-propanediol, 2-methyl-1,3-propanediol, 1,4-butanediol, 1,2-butanediol, 1,5-pentanediol, 2-methyl-1,5-pentanediol, 1,6-hexanediol, neopentylglycol, 2-ethyl-2-butyl-1,3-propanediol, 1,8-octanediol, 1,9-nonanediol, 1,10-decanediol, 2,2,4-trimethyl-1,3-pentanediol, polyethylene glycol, polypropylene glycol, polytetramethylene glycol, trimethylolpropane, trimethylolethane, glycerol, pentaerythritol, bisphenol ethylene oxide adducts, bisphenol propylene oxide adducts, 1,4-cyclohexane dimethanol, 1,4-cyclohexanediol, 1,3-cyclohexane dimethanol, 1,3-cyclohexanediol, hydrogenated bisphenol A, spiroglycol, tricyclodecanediol, tricyclodecane dimethanol, resorcinol, 1,3-bis(2-hydroxyethoxy)benzene, and the like.

The polyester may be obtained by a known method such as melt polymerization method, solution polymerization method, and solid-state polymerization method.

The hydrophilic group may be introduced by a known method. In a case of introducing $-COO^-$, a method is applied in which a polycondensation reaction using, for example, trimellitic anhydride, trimellitic acid, pyromellitic dianhydride, pyromellitic acid, trimesic acid, cyclobutane tetracarboxylic acid, dimethylolpropionic acid, or the like is carried out, and then an amino compound, ammonia or an alkali metal salt is used for neutralization.

The polyvinyl alcohol is usually a resin obtained using a vinyl ester such as vinyl formate, vinyl acetate, vinyl propionate, and vinyl pivalate. For example, a resin obtained by the following method (A) or (B), and further a resin having a primary to tertiary amino group or quaternary ammonium group at the backbone or side chain of a polyvinyl alcohol may be used.
(A) Polyvinyl alcohol obtained by polymerizing a vinyl ester, and then saponifying the polymer
(B) Polyvinyl alcohol obtained by copolymerizing a vinyl ester and an ethylenically unsaturated monomer, and then saponifying the copolymer Examples of the ethylenically unsaturated monomer used in the method (B) include α-olefin such as ethylene, propylene, isopropylene, butylene, isobutylene, pentylene, hexylene, cyclohexylene, cyclohexyl ethylene, and cyclohexyl propylene; acrylic acid, methacrylic acid, (anhydrous) fumaric acid, (anhydrous) maleic acid, (anhydrous) itaconic acid, acrylonitrile, methacrylonitrile, acrylamide, methacrylamide, trimethyl-(3-acrylamide-3-dimethylpropyl)-ammonium chloride, acrylamide-2-methylpropanesulfonic acid and sodium salt thereof, ethyl vinyl ether, butyl vinyl ether, N-vinyl pyrrolidone, vinyl chloride, vinyl bromide, vinyl fluoride, vinylidene chloride, vinylidene fluoride, tetrafluoroethylene, sodium vinylsulfonate, sodium allyl sulfonate, and the like.

Examples of the cellulose include ethyl cellulose, cellulose acetate propionate, cellulose acetate butylate, methyl cellulose, cellulose acetate, cellulose butyrate, and the like.

Examples of the starch include denatured starch such as oxidized starch, etherified starch and esterified starch; and the like.

The polyacrylamide may be obtained copolymerizing an acrylamide (or a methacrylamide), at least one monomer selected from a cationic monomer and an anionic monomer, and other monomer such as a crosslinking agent.

Examples of the polyalkylene oxide include polyethylene oxide, polypropylene oxide, ethylene oxide-propylene oxide copolymer, a polymer obtained reacting any of these polyalkylene oxides with a polycarboxylic acid or its anhydride, or a lower alkyl ester, a polymer obtained reacting any of these polyalkylene oxide with a diisocyanate, and the like.

Examples of the polyvinyl pyrrolidone include a homopolymer of a vinyl pyrrolidone such as N-vinyl-2-pyrrolidone and N-vinyl-4-pyrrolidone (more specifically, polyvinylpyrrolidone); a copolymer obtained using vinylpyrrolidone and a vinyl monomer; and the like.

Examples of the vinyl monomer include an aliphatic vinyl ester such as vinyl acetate, vinyl propionate and vinyl lactate; a vinyl ether such as cyclohexyl vinyl ether, ethyl vinyl ether, hydroxyethyl vinyl ether, hydroxybutyl vinyl ether, and hydroxycyclohexyl vinyl ether; an acrylate or methacrylate such as methyl acrylate, methyl methacrylate, ethyl acrylate, ethyl methacrylate, 2-hydroxyethyl acrylate, 2-hydroxyethyl methacrylate, 2-hydroxypropyl acrylate, 2-hydroxypropyl methacrylate, 3-hydroxypropyl acrylate and 3-hydroxypropyl methacrylate; an allyl ether such as hydroxybutyl allyl ether and ethylene glycol monoallyl ether; and the like.

A polyester, a poly vinyl alcohol and a cellulose are preferable as the polymer since these polymers are excellent in adhesiveness between the chemical adsorption type deodorizer (X) and a fiber, and a deodorizing mask having the polymer will not emit an unpleasant odor when the deodorizing mask is stored in an enclosed environment, and can be more pleasantly used thereafter.

A solid content of the adhesive composition (namely, a solid content derived from the adhesive composition) in the deodorizing fiber layer (L1) is preferably in a range from 10 to 200 parts by mass, more preferably from 30 to 100 parts by mass, and further preferably 40 to 60 parts by mass based on 100 parts by mass of the deodorizer containing the chemical adsorption type deodorizer (X).

In the deodorizing fiber layer (L1), the higher the proportion of the solid content of the adhesive composition to the chemical adsorption type deodorizer (X), the higher the adhesion of the chemical adsorption type deodorizer (X) to the fiber surface, and thus the more highly dropping is prevented. On the other hand, when the proportion of the solid content of the adhesive composition is low, the chemical adsorption type deodorizer (X) is more easily exposed. The chemical adsorption type deodorizer (X) readily contacts with the malodorous component contained in the malodorous gas, and marked deodorizing effect is achieved. Accordingly, in order to efficiently achieve marked deodorizing effect by exposing the chemical adsorption type deodorizer (X) while preventing it dropping, the content ratio of the solid content in the adhesive composition and the chemical adsorption type deodorizer (X) is preferably 10% to 90% by mass and 10% to 90% by mass, and more preferably 20% to 50% by mass and 50% to 80% by mass, respectively, based on 100% by mass of a total of them.

An air permeability in the deodorizing fiber layer (L1) is preferably in a range of 40 to 400 $cm^3/(cm^2 \cdot s)$, more preferably from 60 to 350 $cm^3/(cm^2 \cdot s)$, and further preferably 100 to 300 $cm^3/(cm^2 \cdot s)$ for sufficiently achieving deodorizing effect.

A basis weight of the deodorizing fiber layer (L1) is preferably in a range from 15 to 100 $g/m^2$, more preferably from 20 to 90 $g/m^2$, and further preferably from 30 to 80 $g/m^2$ for sufficiently achieving permeability and deodorizing effect in the main body part.

Next, the deodorizing fiber layer (L2) and fiber layer (L3) provided as necessary are described. The deodorizing fiber layer (L2) contains a composite fiber having other chemical adsorption type deodorizer bonded to a surface of a fiber with an adhesive, and may have the similar structure as the deodorizing fiber layer (L1) except that the deodorizer is different. When the main body part includes the deodorizing fiber layer (L2), the number of the deodorizing fiber layer (L2) is not particularly limited and may be composed of one or more layers.

A content of the other chemical adsorption type deodorizer in the deodorizing fiber layer (L2) is preferably 1 $g/m^2$ or more, more preferably 3 $g/m^2$ or more, and further preferably 5 $g/m^2$ or more. The upper limit is usually 30 $g/m^2$ since air permeability in the deodorizing fiber layer (L2) decreases as the content of the other chemical adsorption type deodorizer in the deodorizing fiber layer (L2) increases. In addition, a content ratio of the other chemical adsorption type deodorizer is preferably in a range from 2 to 60 parts by mass, more preferably from 5 to 50 parts by mass, and further preferably from 10 to 40 parts by mass based on 100 parts by mass of the fibers constituting the deodorizing fiber layer (L2).

An air permeability in the deodorizing fiber layer (L2) is preferably in a range from 40 to 400 $cm^3/(cm^2 \cdot s)$, more preferably from 60 to 350 $cm^3/(cm^2 \cdot s)$, and further preferably 100 to 300 $cm^3/(cm^2 \cdot s)$ for sufficiently achieving deodorizing effect.

A basis weight of the deodorizing fiber layer (L2) is preferably in a range from 15 to 100 $g/m^2$, more preferably from 20 to 90 $g/m^2$, and further preferably from 30 to 80 $g/m^2$ for sufficiently achieving permeability and deodorizing effect in the main body part.

The fiber layer (L3) is a layer containing no deodorizer or component that imparts other function, and may have the similar structure as the deodorizing fiber layer (L1) except that it is composed solely of fibers. The fiber layer (L3) can be used as, for example, a protective layer or dust preventive layer for the deodorizing fiber layers (L1) and (L2).

An air permeability in the fiber layer (L3) is preferably in a range from 40 to 400 $cm^3/(cm^2 \cdot s)$, more preferably from 50 to 300 $cm^3/(cm^2 \cdot s)$, and further preferably from 60 to 250 $cm^3/(cm^2 \cdot s)$ for sufficiently achieving permeability without reducing the deodorizing effect. When the fiber layer (L3) is used as a dust preventive layer, the air permeability in the fiber layer (L3) is preferably lower than the air permeability in the deodorizing fiber layer (L1).

A basis weight of the fiber layer (L3) is preferably in a range from 10 to 60 $g/m^2$, more preferably from 15 to 50 $g/m^2$, and further preferably from 20 to 40 $g/m^2$ for sufficiently achieving permeability in the main body part.

In the deodorizing mask of the present invention, when an air permeability of the main body part containing the deodorizing fiber layer (L1) is high, a wearer breaths easily, but the reactivity between a malodorous gas and the chemical adsorption type deodorizer (X) is lowered. The air permeability of the main body part is preferably in a range from 20 to 80 $cm^3/(cm^2 \cdot s)$, and more preferably from 25 to 50 $cm^3/(cm^2 \cdot s)$. Using such a deodorizing mask, marked deodorizing performance to a sulfur-based malodorous gas is achieved, and clear air is inhaled during the use of the mask.

Figure 1:
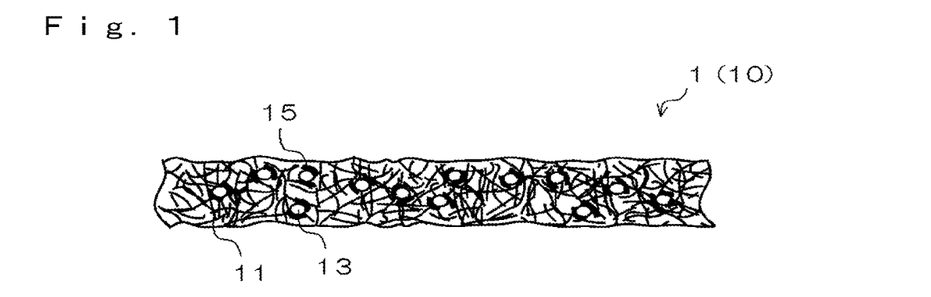
FIG. 1 is a schematic cross sectional view showing one example of the main body part consisting of a deodorizing fiber layer constituting the deodorizing mask.
Figure 2:
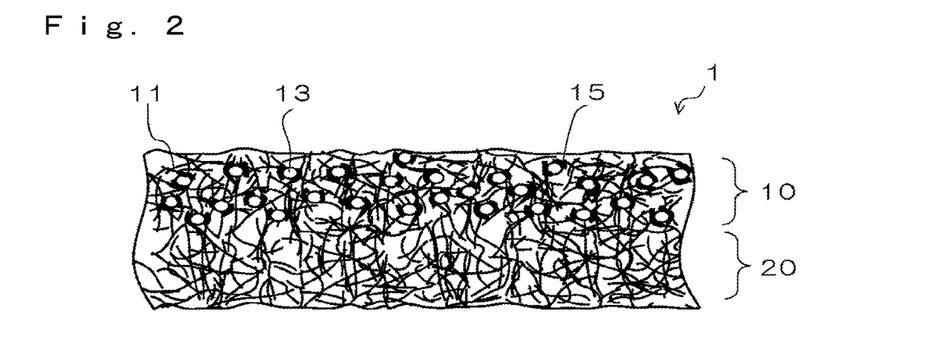
FIG. 2 is a schematic cross sectional view showing other example of the main body part consisting of a deodorizing fiber layer constituting the deodorizing mask.
Figure 3:
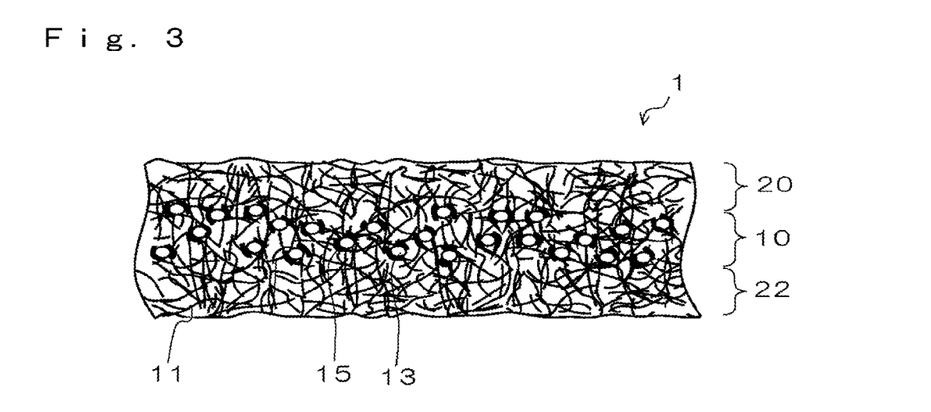
FIG. 3 is a schematic cross sectional view showing other example of the main body part consisting of a deodorizing fiber layer constituting the deodorizing mask.

Examples of the main body part according to the present invention are shown in FIGS. 1 to 3.

FIG. 1 shows a mask main body part 1 consisting of a deodorizing fiber layer (L1) 10, and the mask main body part 1 includes a fiber 11, a chemical adsorption type deodorizer (X) 13, and a joint portion 15 bonding the fiber 11 and chemical adsorption type deodorizer (X) 13 by an adhesive composition. As described above, the deodorizing fiber layer (L1) 10 may contain other chemical adsorption type deodorizer, and also in this case, the fiber 11 and other chemical adsorption type deodorizer are usually bonded by an adhesive composition.

FIG. 2 shows a mask main body part 1 including the deodorizing fiber layer (L1) 10 and other fiber layer 20. The other fiber layer 20 may be the deodorizing fiber layer (L2) or fiber layer (L3).

FIG. 3 shows a mask main body part 1 including other fiber layer 20, the deodorizing fiber layer (L1) 10, and other fiber layer 22 in this order, and the other fiber layer 20 and other fiber layer 22 may be the deodorizing fiber layer (L2) or fiber layer (L3) having identical or different structures.

The main body part 1 may have a flat structure or a three-dimensional structure. When the mask is an omega pleated deodorizing mask having a three-dimensional structure shown in FIG. 5, the mask may have a folded main body part 1 shown in FIG. 4.

The deodorizing mask 100 of the present invention is an article covering the nose and mouth. Therefore the deodorizing mask 100 usually has a member (ear hook) 2 which locks an ear at the backside, or a member (band) 3 which surrounds the back of head at an edge of the main body part 1 (see FIGS. 5, 6 and 7).

Figure 5:
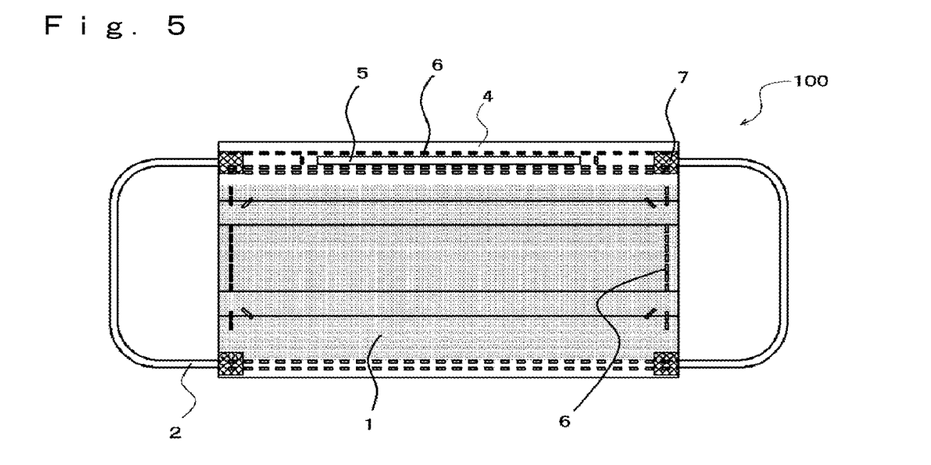
FIG. 5 is a schematic plan view showing one example of a deodorizing mask having the main body part of FIG. 4.
Figure 6:
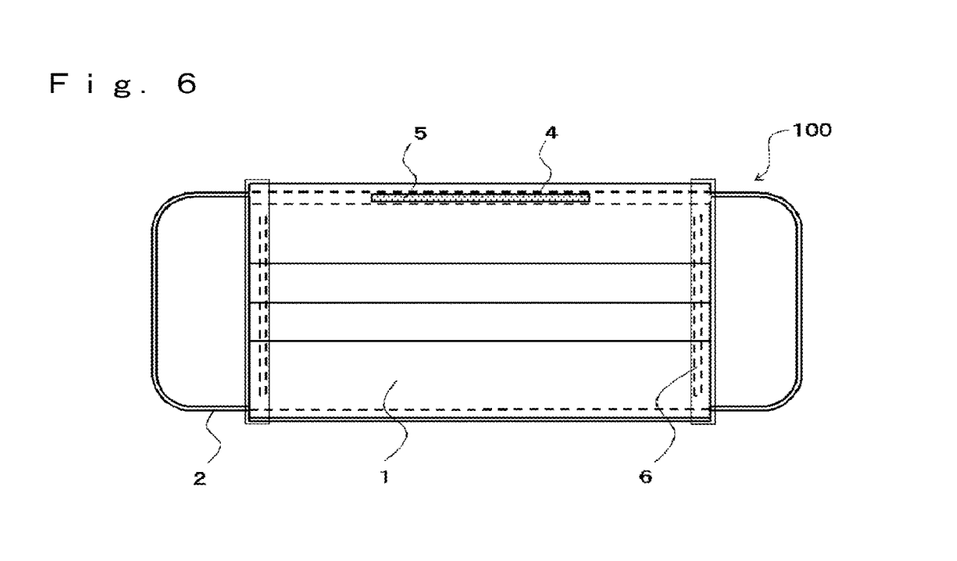
FIG. 6 is a schematic plan view showing other example of a deodorizing mask having a pleated main body part.

The ear hook 2 shown in FIGS. 5 and 6 is provided in a pair of right and left for holding the main body part 1 on the face of the wearer. The ear hook 2 is preferably formed of an elastic member that exerts elastic force in its longitudinal direction. The main body part 1 usually has no elasticity or flexibility, thereby maintaining its shape, so that the elasticity imparted only to the ear hook 2 facilitates secure covering of the nose and mouth by the main body part 1.

Figure 7:
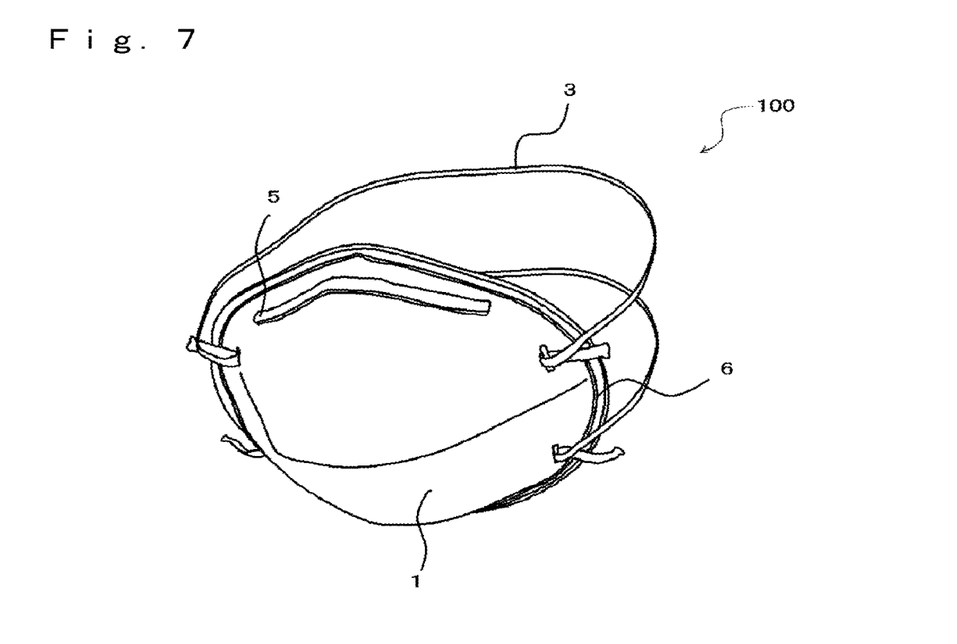
FIG. 7 is a schematic perspective view showing other example of a deodorizing mask.

In addition, the deodorizing mask 100 of the present invention may have a nose wire 5 to more ensure fixation during wearing (see FIGS. 5, 6 and 7). A material for the nose wire 5 is not particularly limited. The material is preferably a metal or resin which has flexibility or softness and imparts shape retentivity since it is easy to conform an upper portion 4 of the main body part to asperities on the face (see FIGS. 5 and 6). The nose wire 5 may be arranged in the main body part 1, or exposed therefrom.

The deodorizing mask of the present invention can be produced by a method including a step of preparing a sheet (S) for the main body part 1 containing the deodorizing fiber layer 10, and a step of processing the sheet (S) into a desired shape. Thereafter, the method may include, as necessary, a step of connecting a member (for ear hook 2) which locks an ear at the backside, or a member (for band 3) which surrounds the back of head, a step of arranging a nose wire, and the like.

In the step of preparing a sheet (S), the following methods can be applied.

(1) A method in which a deodorizer-containing processing liquid containing a chemical adsorption type deodorizer (X) and an adhesive composition is subjected to coating (padding, dipping, coating, spraying, printing or the like) to the whole of a base fabric (woven fabric or nonwoven fabric) consisting of a fiber containing no chemical adsorption type deodorizer, drying is conducted to adhere the chemical adsorption type deodorizer (X) onto a surface of the fiber constituting the base fabric, and a sheet (S) consisting substantially of a deodorizing fiber layer (L1) is obtained.

(2) A method in which a deodorizer-containing processing liquid containing a chemical adsorption type deodorizer (X) and an adhesive composition is subjected to coating (padding, dipping, coating, spraying, printing or the like) to the whole of a base fabric (woven fabric or nonwoven fabric) consisting of a fiber containing no chemical adsorption type deodorizer, drying is conducted to adhere the chemical adsorption type deodorizer (X) onto a surface of the fiber constituting the base fabric to prepare a deodorizing sheet for a deodorizing fiber layer (L1), and the deodorizing sheet and a woven fabric or nonwoven fabric that includes the other fiber containing no chemical adsorption type deodorizer are bonded by using an adhesive, interlacing treatment, or the like to produce a sheet (S) consisting of a deodorizing fiber layer (L1) and the other fiber layer (L3).

(3) A method in which a deodorizer-containing processing liquid containing a chemical adsorption type deodorizer (X) and an adhesive composition is subjected to coating (padding, dipping, coating, spraying, printing or the like) or injecting to a part (one-face side surface layer or an inside alone) in a cross-sectional direction of a base fabric (woven fabric or nonwoven fabric) consisting of a fiber containing no chemical adsorption type deodorizer, drying is conducted to adhere the chemical adsorption type deodorizer (X) onto a surface of the fiber constituting the base fabric, and a sheet (S) consisting of a deodorizing fiber layer (L1) and a fiber layer (L3) containing no deodorizer is obtained.

(4) A method in which a woven fabric or nonwoven fabric consisting of a composite fiber in which a chemical adsorption type deodorizer (X) is buried on a surface of a base portion of the fiber so that the deodorizer is exposed is used or subjected, if necessary, to an interlacing treatment (by needle-punching method, for example), and a sheet (S) consisting substantially of a deodorizing fiber layer (L1) is obtained.

(5) A method in which a woven fabric or nonwoven fabric consisting of a composite fiber in which a chemical adsorption type deodorizer (X) is buried on a surface of a base portion of the fiber so that the deodorizer is exposed and a woven fabric or nonwoven fabric that includes the other fiber containing no deodorizer are bonded by using an adhesive, interlacing treatment, or the like, and a sheet (S) consisting of a deodorizing fiber layer (L1) and the other fiber layer (L3) is obtained.

(6) A method in which a woven fabric or a nonwoven fabric including a fiber containing no deodorizer is subjected to a heat treatment or a chemical treatment, in a state of contacting the chemical adsorption type deodorizer (X), to fix the chemical adsorption type deodorizer (X) to a surface of the fiber, and a sheet (S) consisting substantially of a deodorizing fiber layer (L1) is obtained.

In the present invention, the method (1) that is a spreading processing method is particularly preferred. In a case of preparing a deodorizing fiber layer (L1) that contains the chemical adsorption type deodorizer (X) and other chemical adsorption type deodorizer, a deodorizer-containing processing liquid containing the chemical adsorption type deodorizer (X), other chemical adsorption type deodorizer, and an adhesive is preferably used.

In a case of producing a sheet (S) that includes the deodorizing fiber layer (L2) containing other chemical adsorption type deodorizer, it is preferred that a deodorizing sheet substantially consisting of the deodorizing fiber layer (L2) alone is produced in the same manner as those for the deodorizing fiber layer (L1).

The chemical adsorption type deodorizer and the adhesive composition contained in the deodorizer-containing processing liquid for the method (1) and the like are as already mentioned above. In particular, a median diameter of the chemical adsorption type deodorizer contained in the deodorizer-containing processing liquid is preferably in a range from 0.05 to 100 μm since smooth spreading processing can be carried out. A chemical adsorption type deodorizer having small median diameter is preferable since a surface area per a unit mass becomes larger, deodorization efficiency is improved, spreading processing can be easily carried out, and dropping after the processing is hardly occurred. If a chemical adsorption type deodorizer having a median diameter of less than 0.05 μm is used, there causes inconveniences that the chemical adsorption type deodorizer is buried at an inside of the adhesive layer and not exposed, and that the chemical adsorption type deodorizer causes secondary flocculation at a time of the spreading process and undissolved lumps are formed at a surface of the woven fabric or the nonwoven fabric, which drop after the processing. The median diameter of the chemical adsorption type deodorizer is more preferably in a range from 0.1 to 50 μm, and further preferably from 0.2 to 30 μm.

Depending on the chemical adsorption type deodorizer, a deodorization effect is sometimes lowered by coexisting these proximately in the deodorizing fiber layer. Therefore, when a plural chemical adsorption type deodorizers are to be fixed, it is necessary to select a method in which a deodorizer-containing processing liquid containing a plural types of the chemical adsorption type deodorizer is prepared and the composition is used for spreading processing as it is or a method in which a plural types of deodorizer-containing processing liquids each containing one kind of the chemical adsorption type deodorizer are prepared and spreading processing is carried out repeatedly by using these compositions separately.

In a case where a deodorizer-containing processing liquid containing an adhesive composition and a chemical adsorption type deodorizer is used, higher ratio of a specific polymer in the adhesive composition to the chemical adsorption type deodorizer is preferred from a viewpoint that a fixing force of the chemical adsorption type deodorizer is heightened and dropping of the chemical adsorption type deodorizer is suppressed. On the other hand, when a ratio of the polymer adhesive is low, the chemical adsorption type deodorizer can be easily exposed, and as a result, the chemical adsorption type deodorizer is easily contacted with the malodorous component contained in the malodorous gas whereby an excellent deodorization effect can be obtained. Accordingly, to expose the chemical adsorption type deodorizer with good efficiency and to obtain an excellent deodorization effect, a content ratio of a solid content of the adhesive composition and the chemical adsorption type deodorizer is preferably in a range from 10% to 90% by mass and 10% to 90% by mass, and more preferably 20% to 50% by mass and 50% to 80% by mass, respectively, based on 100% by mass of a total of the solid content of the adhesive composition and the chemical adsorption type deodorizer.

When an additive is added to the deodorizer-containing processing liquid depending on types of polymer in the adhesive composition, a function other than the deodorizing performance can be provided or improvement of the spreading processability, or the like can be done. Examples of the additive include a dispersant, a defoaming agent, a viscosity modifier, a surfactant, a pigment, a dye, a fragrant, an antimicrobial agent, an antiviral agent, an antiallergenic agent, and the like. A formulation amount of the additive is required to be optionally selected so as not to lower the deodorization effect of the chemical adsorption type deodorizer or not affect to the permeability of the deodorization nonwoven fabric.

A spreading processing method using a deodorizer-containing processing liquid containing the chemical adsorption type deodorizer to a base fabric (woven fabric or nonwoven fabric) consisting of fibers having no deodorizers is as mentioned above. The spreading processing by padding method and dipping method allows uniform fixation of the deodorizer on a surface of the base fabric (woven fabric or nonwoven fabric), and increase exposure of the deodorizer to the atmosphere layer surface. Therefore, it is a preferred processing method for efficiently producing a deodorizing sheet for the deodorizing fiber layer (L1) having marked deodorizing performance. Example of the padding method includes pad drying method, pad steam method, and the like. When the resultant base fabric attached with a film is dried to optionally remove a medium of the deodorizer-containing processing liquid, the adhesive composition exhibits the function whereby the chemical adsorption type deodorizer is adhered to the surface of the fiber constituting the base fabric. The chemical adsorption type deodorizer (X) according to the present invention tends to have high hydrous ability. When the deodorizer-containing processing liquid contains water as a medium, removal of water by drying is difficult. Accordingly, in consideration of productivity, the base fabric having a coat must be dried at a high temperature. However, when a temperature exceeding 150° C. is applied to the base fabric having a coat, unpleasant odor may occur. A drying temperature in the step of bonding the deodorizer to fibers by an adhesive component is preferably in a range from 110° C. to 150° C., and more preferably from 120° C. to 140° C. In a case of considering productivity and suppression of the occurrence of unpleasant odor in particular, the drying temperature is further preferably from 123° C. to 138° C. A drying time is not particularly limited, but is preferably in a range from 2 to 10 minutes, and more preferably from 2 to 5 minutes. When the drying is conducted under such conditions, a deodorizing sheet for the deodorizing fiber layer (L1) can be produced.

When a deodorizing sheet for the deodorizing fiber layer 10 is produced using the deodorizer-containing processing liquid, it is preferred to use, as a base fabric, a nonwoven fabric produced by needle-punching method, a nonwoven fabric produced by thermal bonding method or a nonwoven fabric produced by spun bonding method for the purpose of joining the chemical adsorption type deodorizer (X) uniformly to the surface of the fiber constituting the base fabric and making setting of permeability and thickness easy.

In a case of conducting a step of processing the main body part 1 into a desired shape, a step of connecting a member (for ear hook 2) which locks an ear at the backside, or a member (for band 3) which surrounds the back of head, a step of arranging a nose wire, or the other step after preparing the sheet (S), publicly known methods may be applied.

The deodorizing mask of the present invention is suitable for the use in working sites such as excreta treatment facilities, livestock farms, sewage treatment plants, waste treatment facility, garbage treatment facility, fertilizer plants, chemical plants, hospitals, nursing facilities, fishing ports, and disaster sites, and domestic sites where bad smell is emitted during working.

EXAMPLES

Hereinafter, the present invention is specifically described using Examples. The present invention is not limited to the Examples. In the following description, "part(s)" and "%" are based on mass unless otherwise indicated.

1. Material for Deodorizing Mask

As will be described in detail below, the deodorizing mask was produced as follows: a deodorizing nonwoven fabric was prepared using a base fabric consisting of the following nonwoven fabric sheet, and a deodorizer-containing processing liquid including the deodorizer shown in Table 1 and the adhesive composition (aqueous solution or aqueous dispersion) shown in Table 2, and then the deodorizing nonwoven fabric and other nonwoven fabric were used to produce the omega pleated mask shown in FIGS. 4 and 5.

(Nonwoven Fabric Sheet W1)

A nonwoven fabric obtained by subjected fibers containing a polypropylene resin and a polyethylene resin at a mass ratio of 1:1, and polyethylene terephthalate resin fibers at a mass ratio of 1:1 to needle-punch method for interlacing was used.

(Nonwoven Fabric Sheet W2)

A nonwoven fabric obtained by subjected polypropylene resin fibers and polyethylene resin fibers at a mass ratio of 1:1 to thermal bond method was used.

TABLE 1

| Deodorant | Average diameter [μm] | Target malodorous component | Deodorization capacity [mL/g] |
|---|---|---|---|
| CuO•SiO$_2$ composite oxide | 3 | Hydrogen sulfide | 185 |
|  |  | Methyl mercaptan | 48 |
| Copper zirconium phosphate | 1 | Hydrogen sulfide | 110 |
|  |  | Methyl mercaptan | 42 |
| Zinc oxide | 5 | Hydrogen sulfide | 130 |
|  |  | Methyl mercaptan | 15 |
| Amorphous zinc oxide | 10 | Hydrogen sulfide | 110 |
|  |  | Methyl mercaptan | 7 |
| Surface-treated zinc oxide | 1 | Hydrogen sulfide | 110 |
|  |  | Methyl mercaptan | 7 |
| Activated charcoal | 3 | Hydrogen sulfide | 10 |
|  |  | Methyl mercaptan | 4 |
| Titanium oxide | 4 | Hydrogen sulfide | 4 |
|  |  | Methyl mercaptan | 3 |
| Zirconium phosphate | 0.8 | Ammonia | 150 |
| Aluminum silicate | 12 | Ammonia | 34 |
| Hydrous zirconium oxide | 1 | Acetic acid | 32 |
| Hydrotalcite | 5 | Acetic acid | 48 |
| 30% Adipic acid dihydrazide-carried silica gel | 5 | Acetaldehyde | 38 |
| Amorphous zeolite | 4 | Ammonia | 53 |

The average diameter of deodorizers indicated in Table 1 was a median diameter measured with a volume standard using a laser diffraction particle distribution.

A test method for calculating the deodorization capacity of deodorizers is as follows.

In a Tedlar® bag was charged 0.01 g of a deodorizer, and after sealing, 2 L of a gas containing hydrogen sulfide (1600 ppm), methylmercaptan (40 ppm), ammonia (8000 ppm), methylmercaptan (40 ppm), acetic acid (380 ppm) or acetaldehyde (2000 ppm), each of which corresponds to 200-fold of a concentration of the odor intensity of 5 was filled therein. After 24 hours, concentrations (remaining gas component concentrations) of the respective malodorous components were measured with a gas detecting tube and the deodorization capacity (mL/g) was obtained by the following equation.

Deodorization capacity (mL/g)=[2000 (mL)×(Initial malodorous gas component concentration (ppm)−Remaining gas component concentration (ppm))×10$^{-6}$]/0.01 (g)

TABLE 2

| Adhesive composition | Solid content [% by mass] | Average molecular weight | Viscosity [mPa · s/ 20° C.] | Saponification degree [mol %] |
|---|---|---|---|---|
| (S1) Aqueous dispersant of polyester | 25 | 16000 | 25 | — |
| (S2) Aqueous dispersant of polyester | 20 | 14000 | 5 | — |
| (S3) Aqueous solution of poly vinyl alcohol | 10 | — | 1600 | 86-90 |
| (S4) Aqueous solution of poly vinyl alcohol | 10 | — | 2500 | 98-99 |
| (S5) Aqueous solution of cellulose | 2 | — | 4000 | — |
| (S6) Acryl-based emulsion | 50 | 480000 | 50 | — |
| (S7) Acryl-based emulsion | 50 | 350000 | 145 | — |
| (S8) Urethane-based emulsion | 30 | 400000 | 90 | — |

2. Evaluating Method of Deodorizing Mask (1) Air Permeability of Deodorizing Mask The air permeability of deodorizing mask in the cross section direction of the main body part thereof was measured by Frazier method according to JIS L 1096:2010. The unit is cm$^3$/(cm$^2$·s).

(2) Deodorizing Performance of Deodorizing Mask

A measurement of the malodorous component reduction ratio and a sensory test for odor intensity were carried out in the following manner.

(a) Measurement of Malodorous Component Reduction Ratio

The deodorizing test was carried out by passing a malodorous gas prepared so as to contain a malodorous component at a predetermined concentration, through the main body part of the deodorizing mask from one side to the other side. More specifically, a malodorous gas contained in a bag was passed through the deodorizing mask having a passage area of 5 cm$^2$ under aspiration using a gas sampler "MODEL GV-100" (model name) manufactured by Gastec Corporation, and then the concentration of the malodorous component in the passing gas was measured using a gas detecting tube.

As a sulfur-based malodorous gas for the following test, a gas containing hydrogen sulfide (8 ppm) corresponding to an odor intensity of 5 and methyl mercaptan (4 ppm) corresponding to 20-fold of an odor intensity of 5 based on the six-scale odor intensity system was passed. In addition, as other malodorous gas, a gas containing ammonia (40 ppm), acetic acid (1.9 ppm), or acetaldehyde (10 ppm), each of which corresponds to an odor intensity of 5 based on the six-scale odor intensity system was passed.

After ventilation, a gas detecting tube (a gas detecting tube for hydrogen sulfide: No. 70L, a gas detecting tube for methyl mercaptan: No. 4LK, a gas detecting tube for ammonia: No. 3L, a gas detecting tube for acetic acid: No. 81L, a gas detecting tube for acetaldehyde: No. 92L) corresponding to the respective malodorous components was used to measure concentrations of the respective malodorous components in the passing gas. And the malodorous component reduction ratio was obtained by the following equation.

Malodorous component reduction ratio=[(Malodorous component concentration before ventilation−Malodorous component concentration after ventilation)/Malodorous component concentration before ventilation]×100

(b) Sensory Test for Odor Intensity

2 L of a hydrogen sulfide gas (8 ppm) having a concentration of odor intensity 5 was charged into an odor bag, and six subjects smelled the odor in the odor bag to perceive the odor of hydrogen sulfide. Thereafter, the six subjects in a deodorizing mask smelled the odor in the odor bag, and assessed the odor intensity according to the following criteria. The odor intensity of the six subjects was averaged, and recorded as the odor intensity in the sensory test. The smaller the value of the odor intensity, the higher the deodorizing effect of the mask.

Odor intensity 0: odorless
Odor intensity 1: perceivable odor
Odor intensity 2: identifiable weak odor
Odor intensity 3: easily perceivable odor
Odor intensity 4: strong odor
Odor intensity 5: intense odor (3) Evaluation of Odor of Deodorizing Mask Itself and Color Change in Deodorizing Fiber Layer Based on the following (c), (d), and (e), a measurement of the odor concentration, a measurement of the degree of pleasantness, and the like after storage of the deodorizing mask for a certain period were carried out.

(c) Odor Concentration of Deodorizing Mask

Ten deodorizing masks were placed in a sampling bag and sealed, 5 L of odorless air was put thereinto, and the bag was stored in a thermostat at 35° C. for 24 hours or at 50° C. for 30 days. Thereafter, the gas emitted from the masks was collected, and a concentration (odor concentration) was measured by the triangle bag method for odor sensory measurement. The triangle bag method for odor sensory measurement is a method for quantitatively determining the odor intensity using man's sense of smell, and is advantageous in terms of practicality.

The specific method is as follows. Firstly, three polyester bags (volume: 3 L) are given to each of six subjects (smeller). Of the three bags, two bags contain odorless air, and the remaining one bag (Z) contains the gas collected from the mask. The subjects smell the odor of the three gases in the three bags, and identify the bag (Z). Thereafter, the gas in the bag (Z) is diluted with odorless air, and the subjects smell the odor of the three gases in the three bags to identify the bag (Z). The gas in the bag (Z) is diluted stepwise as follows, the same operation is continued, and a dilution ratio when the choice of the bag (Z) by the subject becomes difficult is recorded as the "odor concentration of the deodorizing mask".

An odor concentration of the deodorizing mask was determined using the dilution ratio. The dilution magnification of the gas in the bag (Z) are in the order of 10, 30, 100, 300, 1000, 3000, and 10000 times, and the result used in this experiment is the average of four subjects excluding the one who smelled the most and the one who smelled the least.

The smaller the value of the odor concentration, the closer to the human threshold, and the smaller the odor of the deodorizing mask.

(d) Degree of Pleasantness

Ten deodorizing masks were placed in a sampling bag and sealed, 5 L of odorless air was put thereinto, and the bag was stored in a thermostat at 50° C. for 30 days. Thereafter, the six subjects wore these masks, breathed through the nose five times, and smelled the odor. The quality of the odor was assessed according to the criteria shown in Table 3, and the average of the six subjects was recorded as the result of the evaluation of the degree of pleasantness.

TABLE 3

| Odor quality | Degree of pleasantness |
| --- | --- |
| Extremely unpleasant | −4 |
| Very unpleasant | −3 |
| Unpleasant | −2 |
| Rather unpleasant | −1 |
| Neither pleasant or unpleasant | 0 |
| Rather pleasant | 1 |
| Pleasant | 2 |

TABLE 3-continued

| Odor quality | Degree of pleasantness |
| --- | --- |
| Very pleasant | 3 |
| Extremely pleasant | 4 |

(e) Color Change

A deodorizing mask was placed in a sampling bag and sealed, 5 L of odorless air was put thereinto, and the bag was stored in a thermostat at 50° C. for 30 days. Thereafter, the color difference on a surface of the deodorizing fiber layer was measured using a color difference meter "Σ80" (model name) manufactured by Nidec Corporation, compared with that of a new product, and ΔE was obtained. The smaller the ΔE value, the smaller the degree of color change.

3. Production of Deodorizing Nonwoven Fabric

A deodorizer-containing processing liquid including the deodorizer shown in Table 1 and the adhesive composition (aqueous solution or aqueous dispersion) shown in Table 2 and a base consisting of the above-mentioned nonwoven fabric sheet were used to produce a deodorizing nonwoven fabric for the formation of a deodorizing fiber layer constituting a deodorizing mask.

Production Example 1 (Production of Deodorizing Nonwoven Fabric D1)

A deodorizer-containing processing liquid having a solid concentration of 10% was prepared using a $CuO \cdot SiO_2$ composite oxide powder, a zirconium phosphate powder, and the adhesive composition S1 so that the mass ratio became 6 parts of the $CuO \cdot SiO_2$ composite oxide, 6 parts of zirconium phosphate, and 6 parts of the solid content of polyester resin. Subsequently, the deodorizer-containing processing liquid was subjected to uniform padding to the nonwoven fabric sheet W1 so as to make spread amounts of the $CuO \cdot SiO_2$ composite oxide and zirconium phosphate 6 $g/m^2$ and 6 $g/m^2$, respectively, and dried at 130° C. Thus a deodorizing nonwoven fabric D1 having deodorizers uniformly and entirely bonded from one side of the nonwoven fabric sheet W1 to the other side was obtained (see, Table 4).

Production Example 2 (Production of Deodorizing Nonwoven Fabric D2)

A deodorizer-containing processing liquid having a solid concentration of 10% was prepared using a $CuO \cdot SiO_2$ composite oxide powder, a zirconium phosphate powder, and the adhesive composition S2 so that the mass ratio became 6 parts of the $CuO \cdot SiO_2$ composite oxide, 6 parts of zirconium phosphate, and 6 parts of the solid content of polyester resin. Subsequently, the deodorizer-containing processing liquid was subjected to uniform padding to the nonwoven fabric sheet W2 so as to make spread amounts of the $CuO \cdot SiO_2$ composite oxide and zirconium phosphate 6 $g/m^2$ and 6 $g/m^2$, respectively, and dried at 135° C. Thus a deodorizing nonwoven fabric D2 having deodorizers uniformly and entirely bonded from one side of the nonwoven fabric sheet W2 to the other side was obtained (see, Table 4).

Production Example 3 (Production of Deodorizing Nonwoven Fabric D3)

A deodorizer-containing processing liquid having a solid concentration of 10% was prepared using a $CuO \cdot SiO_2$ composite oxide powder, a hydrous zirconium oxide powder, and the adhesive composition S3 so that the mass ratio became 6 parts of the $CuO.SiO_2$ composite oxide, 5 parts of hydrous zirconium oxide, and 2.2 parts of the solid content of poly vinyl alcohol resin. Subsequently, the deodorizer-containing processing liquid was subjected to uniform padding to the nonwoven fabric sheet W1 so as to make spread amounts of the $CuO.SiO_2$ composite oxide and hydrous zirconium oxide 6 g/m$^2$ and 5 g/m$^2$, respectively, and dried at 135° C. Thus a deodorizing nonwoven fabric D3 having deodorizers uniformly and entirely bonded from one side of the nonwoven fabric sheet W1 to the other side was obtained (see, Table 4).

Production Example 4 (Production of Deodorizing Nonwoven Fabric D4)

A deodorizer-containing processing liquid having a solid concentration of 10% was prepared using a zinc oxide powder, a zirconium phosphate powder, and the adhesive composition S1 so that the mass ratio became 8 parts of zinc oxide, 6 parts of zirconium phosphate, and 7 parts of the solid content of polyester resin. Subsequently, the deodorizer-containing processing liquid was subjected to uniform padding to the nonwoven fabric sheet W2 so as to make spread amounts of zinc oxide and zirconium phosphate 8 g/m$^2$ and 6 g/m$^2$, respectively, and dried at 130° C. Thus a deodorizing nonwoven fabric D4 having deodorizers uniformly and entirely bonded from one side of the nonwoven fabric sheet W2 to the other side was obtained (see, Table 4).

Production Example 5 (Production of Deodorizing Nonwoven Fabric D5)

A deodorizer-containing processing liquid having a solid concentration of 10% was prepared using a zinc oxide powder, a hydrous zirconium oxide powder, and the adhesive composition S1 so that the mass ratio became 8 parts of zinc oxide, 5 parts of hydrous zirconium oxide, and 6.5 parts of the solid content of polyester resin. Subsequently, the deodorizer-containing processing liquid was subjected to uniform padding to the nonwoven fabric sheet W1 so as to make spread amounts of zinc oxide and hydrous zirconium oxide 8 g/m$^2$ and 5 g/m$^2$, respectively, and dried at 125° C. Thus a deodorizing nonwoven fabric D5 having deodorizers uniformly and entirely bonded from one side of the nonwoven fabric sheet W1 to the other side was obtained (see, Table 4).

Production Example 6 (Production of Deodorizing Nonwoven Fabric D6)

A deodorizer-containing processing liquid having a solid concentration of 10% was prepared using a copper zirconium phosphate ($ZrCu(PO_4)_2.H_2O$) powder, an aluminum silicate powder, and the adhesive composition S5 so that the mass ratio became 8 parts of copper zirconium phosphate, 6 parts of aluminum silicate, and 2.8 parts of the solid content of cellulose. Subsequently, the deodorizer-containing processing liquid was subjected to uniform padding to the nonwoven fabric sheet W2 so as to make spread amounts of copper zirconium phosphate and aluminum silicate 8 g/m$^2$ and 6 g/m$^2$, respectively, and dried at 140° C. Thus a deodorizing nonwoven fabric D6 having deodorizers uniformly and entirely bonded from one side of the nonwoven fabric sheet W2 to the other side was obtained (see, Table 4).

Production Example 7 (Production of Deodorizing Nonwoven Fabric D7)

A deodorizer-containing processing liquid having a solid concentration of 10% was prepared using an amorphous zinc oxide powder, a hydrotalcite powder, and the adhesive composition S4 so that the mass ratio became 8 parts of amorphous zinc oxide, 5 parts of hydrotalcite, and 2.6 parts of the solid content of poly vinyl alcohol resin. Subsequently, the deodorizer-containing processing liquid was subjected to uniform padding to the nonwoven fabric sheet W1 so as to make spread amounts of amorphous zinc oxide and hydrotalcite 8 g/m$^2$ and 5 g/m$^2$, respectively, and dried at 135° C. Thus a deodorizing nonwoven fabric D7 having deodorizers uniformly and entirely bonded from one side of the nonwoven fabric sheet W1 to the other side was obtained (see, Table 4).

Production Example 8 (Production of Deodorizing Nonwoven Fabric D8)

A deodorizer-containing processing liquid having a solid concentration of 10% was prepared using a $CuO.SiO_2$ composite oxide powder, a 30% adipic acid dihydrazide-carried silica gel powder, and the adhesive composition S1 so that the mass ratio became 6 parts of the $CuO.SiO_2$ composite oxide, 4 parts of 30% adipic acid dihydrazide-carried silica gel, and 5 parts of the solid content of polyester resin. Subsequently, the deodorizer-containing processing liquid was subjected to uniform padding to the nonwoven fabric sheet W1 so as to make spread amounts of the $CuO.SiO_2$ composite oxide and 30% adipic acid dihydrazide-carried silica gel 6 g/m$^2$ and 4 g/m$^2$, respectively, and dried at 130° C. Thus a deodorizing nonwoven fabric D8 having deodorizers uniformly and entirely bonded from one side of the nonwoven fabric sheet W1 to the other side was obtained (see, Table 4).

Production Example 9 (Production of Deodorizing Nonwoven Fabric D9)

A deodorizer-containing processing liquid having a solid concentration of 10% was prepared using a $CuO.SiO_2$ composite oxide powder, an amorphous zeolite powder, and the adhesive composition S1 so that the mass ratio became 6 parts of the $CuO.SiO_2$ composite oxide, 6 parts of amorphous zeolite, and 6 parts of the solid content of polyester resin. Subsequently, the deodorizer-containing processing liquid was subjected to uniform padding to the nonwoven fabric sheet W2 so as to make spread amounts of the $CuO.SiO_2$ composite oxide and amorphous zeolite 6 g/m$^2$ and 6 g/m$^2$, respectively, and dried at 130° C. Thus a deodorizing nonwoven fabric D9 having deodorizers uniformly and entirely bonded from one side of the nonwoven fabric sheet W2 to the other side was obtained (see, Table 4).

Production Example 10 (Production of Deodorizing Nonwoven Fabric D10)

A deodorizer-containing processing liquid having a solid concentration of 10% was prepared using a surface-treated zinc oxide powder, a 30% adipic acid dihydrazide-carried silica gel powder, and the adhesive composition S2 so that the mass ratio became 8 parts of the surface-treated zinc oxide, 4 parts of 30% adipic acid dihydrazide-carried silica gel, and 6 parts of the solid content of polyester resin. Subsequently, the deodorizer-containing processing liquid was subjected to uniform padding to the nonwoven fabric sheet W1 so as to make spread amounts of the surface-treated zinc oxide and 30% adipic acid dihydrazide-carried silica gel 8 g/m$^2$ and 4 g/m$^2$, respectively, and dried at 135° C. Thus a deodorizing nonwoven fabric D10 having deodorizers uniformly and entirely bonded from one side of the nonwoven fabric sheet W1 to the other side was obtained (see, Table 4).

Production Example 11 (Production of Deodorizing Nonwoven Fabric D11)

A deodorizer-containing processing liquid having a solid concentration of 10% was prepared using a CuO.SiO$_2$ composite oxide powder, a zirconium phosphate powder, and the adhesive composition S6 so that the mass ratio became 6 parts of the CuO.SiO$_2$ composite oxide, 6 parts of zirconium phosphate, and 6 parts of the solid content of acryl-based resin. Subsequently, the deodorizer-containing processing liquid was subjected to uniform padding to the nonwoven fabric sheet W1 so as to make spread amounts of the CuO.SiO$_2$ composite oxide and zirconium phosphate 6 g/m$^2$ and 6 g/m$^2$, respectively, and dried at 130° C. Thus a deodorizing nonwoven fabric D11 having deodorizers uniformly and entirely bonded from one side of the nonwoven fabric sheet W1 to the other side was obtained (see, Table 4).

Production Example 12 (Production of Deodorizing Nonwoven Fabric D12)

A deodorizer-containing processing liquid having a solid concentration of 10% was prepared using a CuO.SiO$_2$ composite oxide powder, a zirconium phosphate powder, and the adhesive composition S8 so that the mass ratio became 6 parts of the CuO.SiO$_2$ composite oxide, 6 parts of zirconium phosphate, and 6 parts of the solid content of urethane-based resin. Subsequently, the deodorizer-containing processing liquid was subjected to uniform padding to the nonwoven fabric sheet W1 so as to make spread amounts of the CuO.SiO$_2$ composite oxide and zirconium phosphate 6 g/m$^2$ and 6 g/m$^2$, respectively, and dried at 130° C. Thus a deodorizing nonwoven fabric D12 having deodorizers uniformly and entirely bonded from one side of the nonwoven fabric sheet W1 to the other side was obtained (see, Table 4).

Production Example 13 (Production of Deodorizing Nonwoven Fabric D13)

A deodorizer-containing processing liquid having a solid concentration of 10% was prepared using a titanium oxide powder, a zirconium phosphate powder, and the adhesive composition S1 so that the mass ratio became 8 parts of titanium oxide, 6 parts of zirconium phosphate, and 7 parts of the solid content of polyester resin. Subsequently, the deodorizer-containing processing liquid was subjected to uniform padding to the nonwoven fabric sheet W1 so as to make spread amounts of titanium oxide and zirconium phosphate 8 g/m$^2$ and 6 g/m$^2$, respectively, and dried at 130° C. Thus a deodorizing nonwoven fabric D13 having deodorizers uniformly and entirely bonded from one side of the nonwoven fabric sheet W1 to the other side was obtained (see, Table 4).

Production Example 14 (Production of Deodorizing Nonwoven Fabric D14)

A deodorizer-containing processing liquid having a solid concentration of 10% was prepared using a titanium oxide powder, a zirconium phosphate powder, and the adhesive composition S6 so that the mass ratio became 8 parts of titanium oxide, 6 parts of zirconium phosphate, and 7 parts of the solid content of acryl-based resin. Subsequently, the deodorizer-containing processing liquid was subjected to uniform padding to the nonwoven fabric sheet W1 so as to make spread amounts of titanium oxide and zirconium phosphate 8 g/m$^2$ and 6 g/m$^2$, respectively, and dried at 135° C. Thus a deodorizing nonwoven fabric D14 having deodorizers uniformly and entirely bonded from one side of the nonwoven fabric sheet W1 to the other side was obtained (see, Table 4).

Production Example 15 (Production of Deodorizing Nonwoven Fabric D15)

A deodorizer-containing processing liquid having a solid concentration of 10% was prepared using an activated charcoal powder, a hydrous zirconium oxide powder, and the adhesive composition S3 so that the mass ratio became 8 parts of activated charcoal, 5 parts of hydrous zirconium oxide, and 2.6 parts of the solid content of poly vinyl alcohol resin. Subsequently, the deodorizer-containing processing liquid was subjected to uniform padding to the nonwoven fabric sheet W1 so as to make spread amounts of activated charcoal and hydrous zirconium oxide 8 g/m$^2$ and 5 g/m$^2$, respectively, and dried at 130° C. Thus a deodorizing nonwoven fabric D15 having deodorizers uniformly and entirely bonded from one side of the nonwoven fabric sheet W1 to the other side was obtained (see, Table 4).

Production Example 16 (Production of Deodorizing Nonwoven Fabric D16)

A deodorizer-containing processing liquid having a solid concentration of 10% was prepared using a zinc oxide powder, an aluminum silicate powder, and the adhesive composition S7 so that the mass ratio became 8 parts of zinc oxide, 6 parts of aluminum silicate, and 7 parts of the solid content of acryl-based resin. Subsequently, the deodorizer-containing processing liquid was subjected to uniform padding to the nonwoven fabric sheet W1 so as to make spread amounts of zinc oxide and aluminum silicate 8 g/m$^2$ and 6 g/m$^2$, respectively, and dried at 130° C. Thus a deodorizing nonwoven fabric D16 having deodorizers uniformly and entirely bonded from one side of the nonwoven fabric sheet W1 to the other side was obtained (see, Table 4).

TABLE 4

| Deodorizing nonwoven | Base | Deodorant | Deodorant spread amount [g/m$^2$] | Adhesive composition |
|---|---|---|---|---|
| Production example 1 | D1 | W1 | CuO•SiO$_2$ composite oxide | 6 | S1 |
| | | | Zirconium phosphate | 6 | |
| Production example 2 | D2 | W2 | CuO•SiO$_2$ composite oxide | 6 | S2 |
| | | | Zirconium phosphate | 6 | |
| Production example 3 | D3 | W1 | CuO•SiO$_2$ composite oxide | 6 | S3 |
| | | | Hydrous zirconium oxide | 5 | |

TABLE 4-continued

| | Deodorizing nonwoven | Base | Deodorant | Deodorant spread amount [g/m²] | Adhesive composition |
|---|---|---|---|---|---|
| Production example 4 | D4 | W2 | Zinc oxide | 8 | S1 |
| | | | Zirconium phosphate | 6 | |
| Production example 5 | D5 | W1 | Zinc oxide | 8 | S1 |
| | | | Hydrous zirconium oxide | 5 | |
| Production example 6 | D6 | W2 | Copper zirconium phosphate | 8 | S5 |
| | | | Aluminum silicate | 6 | |
| Production example 7 | D7 | W1 | Amorphous zinc oxide | 8 | S4 |
| | | | Hydrotalcite | 5 | |
| Production example 8 | D8 | W1 | CuO·SiO₂ composite oxide | 6 | S1 |
| | | | 30% Adipic acid dihydrazide-carried silica gel | 4 | |
| Production example 9 | D9 | W2 | CuO·SiO₂ composite oxide | 6 | S1 |
| | | | Amorphous zeolite | 6 | |
| Production example 10 | D10 | W1 | Surface-treated zinc oxide | 8 | S2 |
| | | | 30% Adipic acid dihydrazide-carried silica gel | 4 | |
| Production example 11 | D11 | W1 | CuO·SiO₂ composite oxide | 6 | S6 |
| | | | Zirconium phosphate | 6 | |
| Production example 12 | D12 | W1 | CuO·SiO₂ composite oxide | 6 | S8 |
| | | | Zirconium phosphate | 6 | |
| Production example 13 | D13 | W1 | Titanium oxide | 8 | S1 |
| | | | Zirconium phosphate | 6 | |
| Production example 14 | D14 | W1 | Titanium oxide | 8 | S6 |
| | | | Zirconium phosphate | 6 | |
| Production example 15 | D15 | W1 | Activated charcoal | 8 | S3 |
| | | | Hydrous zirconium oxide | 5 | |
| Production example 16 | D16 | W1 | Zinc oxide | 8 | S7 |
| | | | Aluminum silicate | 6 | |

4. Production of Deodorizing Mask

The deodorizing nonwoven fabric obtained above, a nonwoven fabric having a basis weight of 25 g/m² obtained by spun bonding method using polypropylene resin fibers (hereinafter referred to as "nonwoven fabric W5"), a nonwoven fabric having a basis weight of 25 g/m² obtained by melt blowing method using polypropylene resin fibers (hereinafter referred to as "dust preventive nonwoven fabric L3"), and a nonwoven fabric having a basis weight of 20 g/m² obtained by spun bonding method using polypropylene resin fibers (hereinafter referred to as "nonwoven fabric W6") were each cut into a piece of 175 mm×165 mm. These pieces were subjected to publicly known production method using the conventional production apparatus, thereby obtaining an omega pleated deodorizing mask 100 having a three-dimensional structure shown in FIGS. 4 and 5. The resultant deodorizing mask was then subjected to various evaluations. The results are shown in Tables 5 to 7.

Example 1 (Production and Evaluation of Deodorizing Mask M1)

Figure 4:
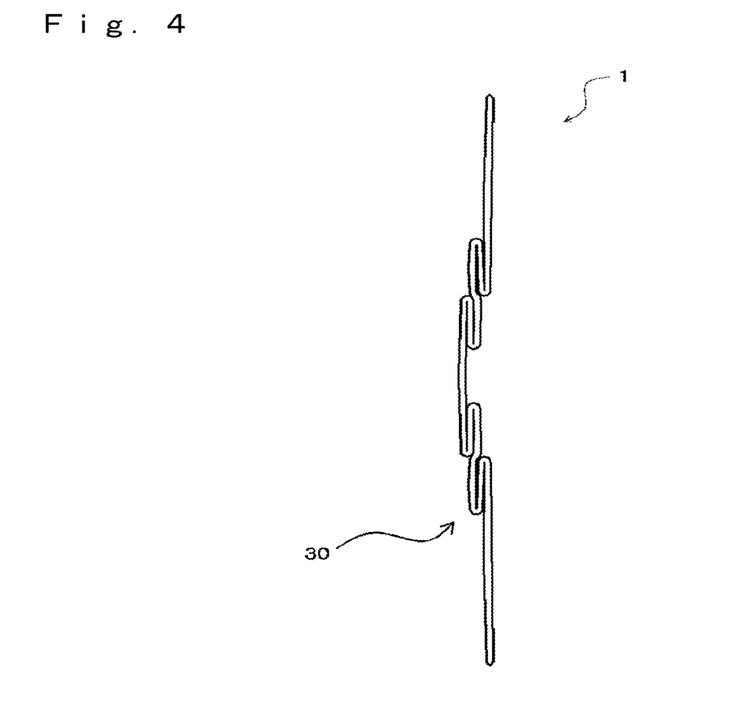
FIG. 4 is a schematic cross sectional view showing one example of a pleated main body part.

The nonwoven fabric W5, the deodorizing nonwoven fabric D1 obtained in Production example 1, the dust preventive nonwoven fabric L3, and the nonwoven fabric W6 were stuck in this order from the outermost layer, and omega pleats 30 were folded to make a rectangle of 175 mm×95 mm (see FIG. 4). Thereafter, a peripheral part of the laminate was welded, with a nose wire 5 inserted into a predetermined position in the mask main body part 1 composed of the laminate. Subsequently, ear hooks 2 were formed by ultrasonic fusion at the both ends of the mask main body part 1, thereby obtaining an omega pleated deodorizing mask M1 having a three-dimensional structure represented by the numeral 100 in FIG. 5.

After that, the resultant deodorizing mask M1 was subjected to an air permeability measurement at the mask main body part 1, a malodorous component reduction ratio measurement of hydrogen sulfide, methyl mercaptan, or ammonia, a sensory test of odor intensity, and an evaluation of the deodorizing mask itself before and after aging. The results are shown in Table 5.

Example 2 (Production and Evaluation of Deodorizing Mask M2)

A deodorizing mask M2 was obtained in the same manner as those in Example 1, except that the deodorizing nonwoven fabric D2 obtained in Production example 2 was used instead of the deodorizing nonwoven fabric D1. After that, the evaluation for the deodorizing mask M2 was carried out in the same manner as those in Example 1. The results are shown in Table 5.

Example 3 (Production and Evaluation of Deodorizing Mask M3)

A deodorizing mask M3 was obtained in the same manner as those in Example 1, except that the deodorizing nonwoven fabric D3 obtained in Production example 3 was used instead of the deodorizing nonwoven fabric D1. After that, the resultant deodorizing mask M3 was subjected to an air permeability measurement at the mask main body part 1, a malodorous component reduction ratio measurement of hydrogen sulfide, methyl mercaptan, or acetic acid, a sensory test of odor intensity, and an evaluation of the deodorizing mask itself before and after aging. The results are shown in Table 5.

Example 4 (Production and Evaluation of Deodorizing Mask M4)

A deodorizing mask M4 was obtained in the same manner as those in Example 1, except that the deodorizing nonwoven fabric D4 obtained in Production example 4 was used instead of the deodorizing nonwoven fabric D1. After that, the evaluation for the deodorizing mask M4 was carried out in the same manner as those in Example 1. The results are shown in Table 5.

Example 5 (Production and Evaluation of Deodorizing Mask M5)

A deodorizing mask M5 was obtained in the same manner as those in Example 1, except that the deodorizing nonwoven fabric D5 obtained in Production example 5 was used instead of the deodorizing nonwoven fabric D1. After that, the evaluation for the deodorizing mask M5 was carried out in the same manner as those in Example 3. The results are shown in Table 5.

Example 6 (Production and Evaluation of Deodorizing Mask M6)

A deodorizing mask M6 was obtained in the same manner as those in Example 1, except that the deodorizing nonwoven fabric D6 obtained in Production example 6 was used instead of the deodorizing nonwoven fabric D1. After that, the evaluation for the deodorizing mask M6 was carried out in the same manner as those in Example 1. The results are shown in Table 6.

Example 7 (Production and Evaluation of Deodorizing Mask M7)

A deodorizing mask M7 was obtained in the same manner as those in Example 1, except that the deodorizing nonwoven fabric D7 obtained in Production example 7 was used instead of the deodorizing nonwoven fabric D1. After that, the evaluation for the deodorizing mask M7 was carried out in the same manner as those in Example 3. The results are shown in Table 6.

Example 8 (Production and Evaluation of Deodorizing Mask M8)

A deodorizing mask M8 was obtained in the same manner as those in Example 1, except that the deodorizing nonwoven fabric D8 obtained in Production example 8 was used instead of the deodorizing nonwoven fabric D1.

After that, the resultant deodorizing mask M8 was subjected to an air permeability measurement at the mask main body part 1, a malodorous component reduction ratio measurement of hydrogen sulfide, methyl mercaptan, or acetaldehyde, a sensory test of odor intensity, and an evaluation of the deodorizing mask itself before and after aging. The results are shown in Table 6.

Example 9 (Production and Evaluation of Deodorizing Mask M9)

A deodorizing mask M9 was obtained in the same manner as those in Example 1, except that the deodorizing nonwoven fabric D9 obtained in Production example 9 was used instead of the deodorizing nonwoven fabric D1. After that, the evaluation for the deodorizing mask M9 was carried out in the same manner as those in Example 1. The results are shown in Table 6.

Example 10 (Production and Evaluation of Deodorizing Mask M10)

A deodorizing mask M10 was obtained in the same manner as those in Example 1, except that the deodorizing nonwoven fabric D10 obtained in Production example 10 was used instead of the deodorizing nonwoven fabric D1. After that, the evaluation for the deodorizing mask M10 was carried out in the same manner as those in Example 8. The results are shown in Table 6.

Comparative Example 1 (Production and Evaluation of Deodorizing Mask M11)

A deodorizing mask M11 was obtained in the same manner as those in Example 1, except that the deodorizing nonwoven fabric D11 obtained in Production example 11 was used instead of the deodorizing nonwoven fabric D1. After that, the evaluation for the deodorizing mask M11 was carried out in the same manner as those in Example 1. The results are shown in Table 7.

Comparative Example 2 (Production and Evaluation of Deodorizing Mask M12)

A deodorizing mask M12 was obtained in the same manner as those in Example 1, except that the deodorizing nonwoven fabric D12 obtained in Production example 12 was used instead of the deodorizing nonwoven fabric D1. After that, the evaluation for the deodorizing mask M12 was carried out in the same manner as those in Example 1. The results are shown in Table 7.

Comparative Example 3 (Production and Evaluation of Deodorizing Mask M13)

A deodorizing mask M13 was obtained in the same manner as those in Example 1, except that the deodorizing nonwoven fabric D13 obtained in Production example 13 was used instead of the deodorizing nonwoven fabric D1. After that, the evaluation for the deodorizing mask M13 was carried out in the same manner as those in Example 1. The results are shown in Table 7.

Comparative Example 4 (Production and Evaluation of Deodorizing Mask M14)

A deodorizing mask M14 was obtained in the same manner as those in Example 1, except that the deodorizing nonwoven fabric D14 obtained in Production example 14 was used instead of the deodorizing nonwoven fabric D1. After that, the evaluation for the deodorizing mask M14 was carried out in the same manner as those in Example 1. The results are shown in Table 7.

Comparative Example 5 (Production and Evaluation of Deodorizing Mask M15)

A deodorizing mask M15 was obtained in the same manner as those in Example 1, except that the deodorizing nonwoven fabric D15 obtained in Production example 15 was used instead of the deodorizing nonwoven fabric D1.

After that, the resultant deodorizing mask M15 was subjected to an air permeability measurement at the mask main body part 1, a malodorous component reduction ratio measurement of hydrogen sulfide, methyl mercaptan, or acetic acid, a sensory test of odor intensity, and an evaluation of the deodorizing mask itself before and after aging. The results are shown in Table 7.

Comparative Example 6 (Production and Evaluation of Deodorizing Mask M16)

A deodorizing mask M16 was obtained in the same manner as those in Example 1, except that the deodorizing nonwoven fabric D16 obtained in Production example 16 was used instead of the deodorizing nonwoven fabric D1. After that, the evaluation for the deodorizing mask M16 was carried out in the same manner as those in Example 1. The results are shown in Table 7.

TABLE 5

| | Deodorizing mask | Permeability [cm³/(cm²·s)] | Target malodorous component | Deodorizing performance Malodorous component reducing ratio [%] | Odor intensity in sensory test | Odor concentration of mask itself After storage at 35° C. for 24 h | After storage at 50° C. for 30 days | Degree of pleasantness | Color change ΔE |
|---|---|---|---|---|---|---|---|---|---|
| Example 1 | M1 | 32.7 | Hydrogen sulfide<br>Methyl mercaptan<br>Ammonia | 96<br>96<br>98 | 0.5 | 41 | 73 | −0.5 | 2.1 |
| Example 2 | M2 | 30.9 | Hydrogen sulfide<br>Methyl mercaptan<br>Ammonia | 98<br>94<br>98 | 0.3 | 55 | 73 | −0.5 | 2.3 |
| Example 3 | M3 | 32.8 | Hydrogen sulfide<br>Methyl mercaptan<br>Acetic acid | 98<br>94<br>>94 | 0.5 | 31 | 55 | −0.3 | 3.2 |
| Example 4 | M4 | 30.1 | Hydrogen sulfide<br>Methyl mercaptan<br>Ammonia | 90<br>84<br>98 | 0.8 | 41 | 73 | −0.7 | 1.7 |
| Example 5 | M5 | 32.0 | Hydrogen sulfide<br>Methyl mercaptan<br>Acetic acid | 90<br>82<br>>94 | 0.8 | 41 | 55 | −0.7 | 1.8 |

TABLE 6

| | Deodorizing mask | Permeability [cm³/(cm²·s)] | Target malodorous component | Deodorizing performance Malodorous component reducing ratio [%] | Odor intensity in sensory test | Odor concentration of mask itself After storage at 35° C. for 24 h | After storage at 50° C. for 30 days | Degree of pleasantness | Color change ΔE |
|---|---|---|---|---|---|---|---|---|---|
| Example 6 | M6 | 30.2 | Hydrogen sulfide<br>Methyl mercaptan<br>Ammonia | 94<br>90<br>84 | 1.0 | 31 | 55 | −0.5 | 2.5 |
| Example 7 | M7 | 31.9 | Hydrogen sulfide<br>Methyl mercaptan<br>Acetic acid | 90<br>80<br>>94 | 1.0 | 73 | 97 | −0.3 | 2.8 |
| Example 8 | M8 | 33.0 | Hydrogen sulfide<br>Methyl mercaptan<br>Acetaldehyde | 96<br>98<br>90 | 0.3 | 55 | 73 | −0.7 | 2.4 |
| Example 9 | M9 | 31.5 | Hydrogen sulfide<br>Methyl mercaptan<br>Ammonia | 96<br>94<br>90 | 0.5 | 41 | 73 | −0.5 | 2.5 |
| Example 10 | M10 | 32.2 | Hydrogen sulfide<br>Methyl mercaptan<br>Acetaldehyde | 90<br>80<br>88 | 1.2 | 55 | 73 | −0.7 | 1.7 |

TABLE 7

| | Deodorizing mask | Permeability [cm³/(cm²·s)] | Target malodorous component | Deodorizing performance Malodorous component reducing ratio [%] | Odor intensity in sensory test | Odor concentration of mask itself After storage at 35° C. for 24 h | After storage at 50° C. for 30 days | Degree of pleasantness | Color change ΔE |
|---|---|---|---|---|---|---|---|---|---|
| Comparative example 1 | M11 | 32.5 | Hydrogen sulfide<br>Methyl mercaptan<br>Ammonia | 94<br>94<br>98 | 0.3 | 548 | 1732 | −2.0 | 10.9 |
| Comparative example 2 | M12 | 32.8 | Hydrogen sulfide<br>Methyl mercaptan<br>Ammonia | 92<br>92<br>96 | 0.5 | 730 | 2310 | −2.7 | 11.4 |
| Comparative example 3 | M13 | 31.0 | Hydrogen sulfide<br>Methyl mercaptan<br>Ammonia | 18<br>14<br>18 | 4.3 | 41 | 73 | −0.7 | 2.4 |

TABLE 7-continued

| | Deodorizing mask | Permeability [cm³/(cm² · s)] | Deodorizing performance | | Odor intensity in sensory test | Odor concentration of mask itself | | Degree of pleasantness | Color change ΔE |
| | | | Target malodorous component | Malodorous component reducing ratio [%] | | After storage at 35° C. for 24 h | After storage at 50° C. for 30 days | | |
|---|---|---|---|---|---|---|---|---|---|
| Comparative example 4 | M14 | 31.9 | Hydrogen sulfide Methyl mercaptan Ammonia | 22 18 20 | 4.5 | 411 | 1732 | −2.3 | 10.5 |
| Comparative example 5 | M15 | 32.0 | Hydrogen sulfide Methyl mercaptan Acetic acid | 38 42 >94 | 4.5 | 55 | 73 | −0.5 | 2.7 |
| Comparative example 6 | M16 | 31.2 | Hydrogen sulfide Methyl mercaptan Ammonia | 88 80 82 | 1.0 | 411 | 1299 | −2.2 | 10.2 |

Tables 5 to 7 indicate the followings. In all of Examples 1 to 10, high deodorizing performance of a malodorous component reduction ratio of 80% or more was exhibited, and in the sensory test, the malodorous component was reduced to the odor intensity closed to odorless, or 1.2 or less. On the other hand, Comparative Examples 3 to 5 were ones using a sulfur-based gas adsorbing deodorizer which was not a chemical adsorption type deodorizer, in the deodorizing fiber layer, and the deodorizing performance was poor as well as the malodorous component reduction ratio and sensory test odor intensity. In Examples 1 to 10, the odor concentration was 100 or less after storage at 35° C. for 24 hours and 50° C. for 30 days, and the degree of pleasantness was −1 or more. The color difference ΔE was 3.2 or less, and the color scarcely changed. On the other hand, in Comparative Examples 1, 2, 4, and 6, the adhesive not included in the present invention was used in the deodorizing fiber layer, and the odor concentration after storage at 35° C. for 24 hours was 400 or more, and the odor concentration after storage at 50° C. for 30 days was 1200 or more, and the degree of pleasantness was −2 or less. In Comparative Examples 1, 2, 4 and 6, the odor concentration after storage at 50° C. for 30 days was increased to three times or more the odor intensity after storage at 35° C. for 24 hours, and the value of color difference ΔE was 10 or more, and the color change was remarkable.

From the above results, the achievement of high sulfur-based gas deodorizing performance by a deodorizing mask requires the use of a chemical adsorption type deodorizer which adsorbs a sulfur-based gas in the deodorizing fiber layer. Furthermore, the reduction of the odor of the deodorizing mask itself, the suppression of the amplification of the odor of the deodorizing mask itself, and the reduction of color change requires the adhesion of a chemical adsorption type deodorizer which adsorbs a sulfur-based gas to fibers by a specific adhesive.

INDUSTRIAL APPLICABILITY

The deodorizing mask of the present invention instantaneously achieves high deodorizing performance for malodorous components in a sulfur-based malodorous gas such as a putrefactive odor passing through the deodorizing fiber layer, the components being containing hydrogen sulfide, mercaptans, dimethyl disulfide, and sulfur-based dioxide. Accordingly, the deodorizing mask is effectively useful in work sites such as excreta treatment facilities, livestock farms, sewage treatment plants, waste treatment facility, garbage treatment facility, fertilizer plants, chemical plants, hospitals, nursing facilities, fishing ports, and disaster sites, and domestic sites where bad smell is emitted during working.

REFERENCE SIGNS LIST

1: mask main body part, 2: ear book, 3: band, 4: upper part of main body part, 5: nose wire, 6: heat seal seam, 7: heat seal mesh, 10: deodorizing fiber layer, 11: fiber, 13: chemical adsorption type deodorizer, 15: joint portion (adhesive composition), 20: other fiber layer, 22: other fiber layer, 30: pleat, 100: deodorizing mask

What is claimed is:
1. A deodorizing mask, comprising:
a main body part comprising a deodorizing fiber layer comprising a composite fiber having a chemical adsorption type deodorizer bonded to a surface of a fiber with an adhesive composition,
wherein the chemical adsorption type deodorizer is a component comprising at least one element selected from the group consisting of a copper element and a zinc element, and
the adhesive composition comprises at least one selected from the group consisting of a polyester, a poly vinyl alcohol, a cellulose, a starch, a poly acrylamide, a poly alkylene oxide and a poly vinyl pyrrolidone.
2. The deodorizing mask according to claim 1, wherein the chemical adsorption type deodorizer is at least one component selected from the group consisting of an oxide comprising a copper element and a phosphate comprising a copper element.
3. The deodorizing mask according to claim 1, wherein a content of the chemical adsorption type deodorizer in the deodorizing fiber layer is not less than 1 g/m².
4. The deodorizing mask according to claim 1, wherein a solid content of the adhesive composition and the chemical adsorption type deodorizer in the deodorizing fiber layer are respectively 10% to 90% by mass and 10% to 90% by mass based on 100% by mass of a total of these components.
5. The deodorizing mask according to claim 1,
wherein a fiber constituting the deodorizing fiber layer comprises a fiber comprising a polyethylene resin, and
wherein a content ratio of the polyethylene resin is in a range from 10% to 80% by mass based on a total amount of fibers constituting the deodorizing fiber layer.
6. The deodorizing mask according to claim 1, wherein the deodorizing fiber layer is a layer in which the chemical adsorption type deodorizer is joined to the surface of the fiber by padding method or dipping method.

7. The deodorizing mask according to claim 1, wherein the adhesive composition comprises at least one selected from the group consisting of a polyester, a poly vinyl alcohol and a cellulose.

\* \* \* \* \*